United States Patent [19]

Jankewitz

[11] 4,452,262

[45] Jun. 5, 1984

[54] METHOD OF APPLYING COSMETICS AND MEDIUM AND DEVICE FOR PERFORMING THE METHOD

[75] Inventor: Axel Jankewitz, Fürth-Oberfürberg, Fed. Rep. of Germany

[73] Assignee: A. W. Faber-Castell, Nürnberg, Fed. Rep. of Germany

[21] Appl. No.: 304,045

[22] Filed: Sep. 21, 1981

[51] Int. Cl.³ .............................................. A45D 40/30
[52] U.S. Cl. .................................................. 132/88.5
[58] Field of Search ....................... 132/88.5, 88.7, 79; 401/198, 59, 11, 58, 60–62; 222/390

[56] References Cited

U.S. PATENT DOCUMENTS

| | | | |
|---|---|---|---|
| 2,064,556 | 12/1936 | Reutter | 401/59 |
| 2,374,065 | 4/1945 | Worthington | 132/88.7 UX |
| 3,369,543 | 2/1968 | Ronco | 401/198 |
| 3,468,612 | 9/1967 | Aston | 132/88.7 X |
| 3,630,211 | 12/1971 | Seidler | 132/88.5 |

OTHER PUBLICATIONS

Edward Sagarin–Cosmetics–1957–150, 159, 171, 183.

*Primary Examiner*—Gregory E. McNeill
*Attorney, Agent, or Firm*—Michael J. Striker

[57] ABSTRACT

A method of applying cosmetics onto skin includes applying onto the skin a pin-shaped coloring cosmetic substance containing a fat or an oil, and wetting the skin with a skin-compatible, slowly evaporating solving medium for the fat or oil of the cosmetic substance. The solving medium comprises 70–90% by weight of aliphatic saturated hydrocarbon with 6–12 C-atoms, and 5–30% by weight of at least one fat-reversing substance. A device for wetting has a container, a tampon soaked with a solving medium and accommodated in the container, a wick arranged in liquid-conducting communication with the tampon and extending outwardly beyond the container, and a sealingly closing cover removable from the container for use of the device.

5 Claims, 2 Drawing Figures

METHOD OF APPLYING COSMETICS AND MEDIUM AND DEVICE FOR PERFORMING THE METHOD

BACKGROUND OF THE INVENTION

The present invention relates to a method of applying a pin-shaped coloring cosmetic substance onto the skin, as well as to a medium and a device for performing the method.

It is known to manufacture and use coloring cosmetics, or so-called make-up, in pin-shaped form. Such pin-shaped cosmetics are used, for example, as a lip pencil, eyelid pencil, eyelash pencil and the like. These articles have different compositions in dependence upon the requirements made thereto, and their composition determines their hardness and thereby the sharpness of lines drawn by them. The above-mentioned cosmetic pins or pencils are utilized in the first place for simultaneous coloring of more or less great surfaces, such as for example lipsticks, eyelid shadow pencils, and the like. They have a relatively soft pin consistency which is obtained by addition of oily or fatty material. In addition to this, the pins have more or less greater quantities of wax or wax-like material which is utilized for providing a sufficient shape stability. The increased shape stability is connected in all cases with the reduced softness. This dependence is so limiting that the pins which are utilized for particularly sharp lines, such as for example so-called "eyeliners" practically cannot be used for homogeneous surface coloring.

The utilization of the known make-up pencils or pins and the application of professional make-up depend on the considerable requirements made to the ability and reliability of a person applying the make-up. This is especially true in the professional field where, for example, an actor or a model must be made up in accordance with the required theme or illumination. When the make-up is applied incorrectly, it is necessary to remove the applied make-up completely or only in wrong regions and with line sharpness if impossible. Cotton bars or cellulose fabric wound in small tampons, which are soaked with a cosmetic oil or the like, are utilized as a rule for these purposes. These auxiliary means often cannot provide for the desired make-up in failure-free manner and without visible correction traces.

SUMMARY OF THE INVENTION

Accordingly, it is an object of the present invention to provide a device for applying a coloring cosmetic substance which, regardless of its consistency, can produce any colored and limited color surface or line. The term "any colored" color surface also includes replaceable or gradually fading coloring.

In keeping with these objects and with others which will become apparent hereinafter, one feature of the present invention resides, briefly stated, in a method of applying cosmetics onto skin, in accordance with which a pin-shaped coloring cosmetic substance containing a fat or an oil is applied onto the skin, and the skin is wetted before or after application of the cosmetic substance with a skin-compatible slowly evaporating solving medium for the fat or oil of the cosmetic substance.

A solving medium for wetting the skin before or after application of a pin-shaped coloring cosmetic substance comprises (in percent by weight): 70-90 of aliphatic saturated hydrocarbon with 6-12 C-atoms, and 5-30 of at least one fat-reversing substance.

A device for wetting the skin with a solving medium before or after application of a pin-shaped coloring cosmetic substance includes a container, a tampon soaked with a solving medium and accommodated in the container, a wick arranged in liquid-conducting communication with the tampon and extending outwardly beyond the container, and a sealingly closing cover removable from the container for use of the device.

The novel features which are considered characteristic for the invention are set forth in particular in the appended claims. The invention itself, however, both as to its construction and its methods of operation, together with additional objects and advantages thereof, will be best understood from the following description of specific embodiments when read in connection with the accompanying drawing.

DESCRIPTION OF A PREFERRED EMBODIMENT

Figure 1:
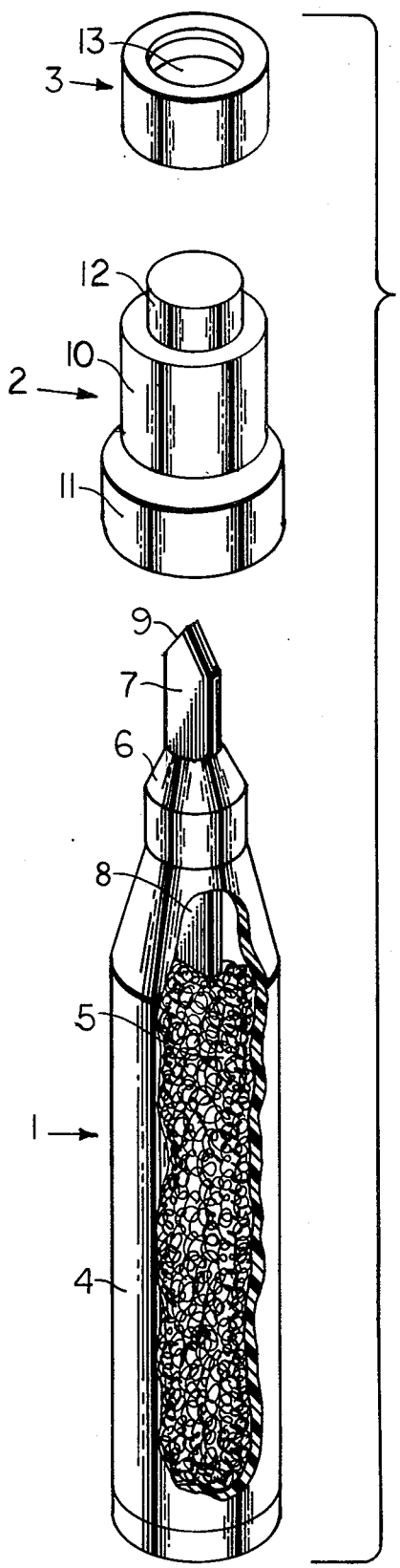
FIG. 1 is an exploded perspective view of a device for wetting the skin with a solving medium before or after applying a coloring cosmetic substance, in accordance with the present invention.

In accordance with a method of applying cosmetics onto the skin, a pin-shaped coloring cosmetic substance containing a fat or an oil is applied onto the skin. A skin-compatible slowly evaporating solving medium for the fat or oil of the cosmetic substance wets the skin before or after the application of the coloring cosmetic substance. The method differs in principle from known methods in the fact that not only the make-up proper is applied, but also additionally a further auxiliary medium is used which is applied separately from the make-up.

When the method of the present invention is performed, it is possible to use make-up pencils or pins which are hard and thereby draw sharp lines, for producing homogeneous and progressively colored surfaces.

Portions of the skin to be treated can first be treated with the slowly evaporating solving medium, and immediately after this, as long as the solving medium is on the skin, the pin-shaped coloring cosmetic substance can be applied as lines or as surfaces. The cosmetic substance can be rubbed into the skin. The solving medium applied on the skin provides for the action in that the cosmetic oil or fat in the sharply drawing pin or pencil is solved and thereby the rather hard pin becomes softer. As a result of this, it is possible to spread by rubbing the make-up extremely uniformly and with regard to the color shadow or color thickness.

In accordance with the invention, a solving medium which is utilized for the pin-shaped cosmetic substance has the following composition (in percent by weight):
40-60 of wax;
5-30 of oil or fat; and
10-30 of paint or pigment.

The above-described method is used, in the first place, for homogeneous and progressively colored great surfaces. When a softer pin or pencil, for example a lipstick, an eyelid shadow pencil, or the like, is utilized from the beginning, the inventive method provides for the possibility to sharply limit the surface which is uniformly colored with this pin or pencil. This is performed without additional auxiliary means. In accordance with the invention it is possible to treat the portion of the skin first with the coloring cosmetic, as usual, and after this to wipe the edges or desired parts of the treated surface with the slowly evaporating solving medium. In this manner, sharp limits can be obtained.

It is also possible to leave untouched predetermined parts or lines in accordance with a pattern inside a surface, and to remove in this part the applied make-up. This situation can take place when, for example, within a predetermined make-up a blue eyelid line is desired. When this eyelid line is produced by a line of a different color, for example a green line, the previously asp plied color must be first removed without destruction of the make-up pattern. The inventive method carries out this in the above-described manner.

A solving medium for implementing the inventive method may have the following composition (in percent by weight):

70–90 of aliphatic saturated hydrocarbon with 6–12 C-atoms; and

5–30 of one or more fat-reversing substances.

Instead of the above-described solving medium, other media can be utilized such as for example high-boiling esters, high-boiling alcohols such as isopropyl alcohol, benzyl alcohol and the like, or also glycol monoethyl ether or similar substances. The fat-reversing substances can be such as isopropylmyristate, lanolin oil, butylstearate, and the like.

A device in accordance with the present invention for implementing the inventive method is shown in FIG. 1 and has a main part 1 including a supply container 4 which can be composed of a synthetic plastic material or metal. A tampon 5 is arranged in the interior of the container 4. The tampon is soaked with a solving medium. The tampon can be composed of a fiber filling; on the other hand, it also can be composed of a foam material with open cells.

The supply container 4 in accordance with the illustrated example is shaped as an upwardly decreasing pipe with a circular cross section. It is to be understood that the supply container 4 may have any other shape. The supply container 4 has an upper part 6 which is neck-shaped.

A wick 7 is arranged in the supply container 4 so that its portion extends upwardly beyond the neck-shaped upper part 6 of the supply container 4. The wick 7 has a length such that its lower end 8 engages into the tampon 5. Thus, the outwardly extending wick is in liquid-conducting communication with the tampon. It is especially advantageous when the wick is exchangeable.

In order to make easier the utilization of the device, the wick 7 has a tip 9 with an inclined wedge-like shape. This shape is particularly advantageous when it is necessary to draw both straight and curved lines. This also makes it possible to treat both sharp linear recesses in the made-up area, and also simultaneously to treat wide zones.

When the device is not used, the wick 7 must be light-tightly closed from the surroundings so as to prevent evaporation of the solving medium. For this purpose, a cover identified by reference numeral 2 is provided. The cover includes a tubular part 10. Facet surfaces 11 are further formed on the cover 2 for gripping purposes. The interior of the tubular part 10 of the cover 2 is so designed that it can be fitted onto the upper neck 6 of the main part 1 in light-tight manner. This is actually known in wick-type writing implements; however, it should be emphasized that the inventive device is not a writing implement for writing with ink or other coloring liquids, but instead is a device for supplying a solving medium which does not write, draw, or the like.

In contrast to the known constructions of covers, the cover 2 has an upper trunnion 12 with an outer diameter which is smaller than the outer diameter of the part 10 of the cover. The axial trunnion 12 is formed for the purposes to be explained hereinbelow.

During the use of the device, the wick 7 is of course dirtied. For cleaning the wick 7, a suction pad 13 is provided. The suction pad 13 is arranged in the interior of a suction pad ring 3. The suction pad 3 can be fitted onto the axial trunnion 12 of the cover 2. The suction pad can be composed of a soft foam material, such as for example polyurethane soft foam, or of a synthetically bonded wool material on a cellulose, rayon, cotton or linter base.

Figure 2:
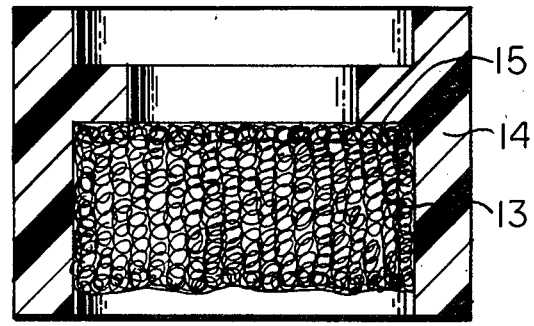
FIG. 2 is a view showing a section of a suction pad ring of the inventive device.

The suction pad ring 3 is shown in FIG. 2 in a longitudinal section. As can be seen from this Figure, the ring 3 has a substantially cylindrical part 14 which is provided in its interior with a ring-shaped constriction 15. The suction pad 13 is inserted into the ring 3 until it abuts against the ring-shaped constriction 15, and is retained in the inserted position in the ring 3. As can be seen from the drawing, the suction pad 13 can be easily exchanged for a new one.

The device in accordance with the present invention operates in the following manner:

In the condition of non-use, the cover 2 is fitted onto the main part 1. In order to start use, the cover 2 is removed from the main part 1. If the tip 9 of the wick 7 is dirty, or when it is dirtied by the make-up during use of the device, the make-up is removed from the tip 9 of the wick 7 with the aid of the suction pad 13. By contacting the suction pad with the tip 9 of the wick 7, a lighter solving medium stream flows from the wick 7 into the suction pad 13. This stream flushes the particles of make-up adhered to the wick. The suction pad 13 is soaked during this step with the solving medium and make-up residues. After termination of the cleaning step, the solving medium evaporates and the suction pad 13 is ready for the next cleaning. The thus cleaned wick 7, which is in constant liquid-conducting communication with the tampon 5, wets the skin with the skin-compatible, slowly evaporating solving medium before or after the application onto the skin of a pin-shaped coloring cosmetic substance.

It will be understood that each of the elements described above, or two or more together, may also find a useful application in other types of constructions differing from the types described above.

While the invention has been illustrated and described as embodied in a method of applying cosmetics onto the skin, as well as a substance and a device for this method, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for wetting skin with a solving medium before or after application of a pin-shaped coloring cosmetic substance, the device comprising a container;

a tampon soaked with a solving medium and accommodated in said container;

a wick arranged in a liquid-conducting communication with said tampon and extending outwardly beyond said container;

a sealingly closing cover movable between an open position in which it is removed from said container for use of the device and a closed position in which it closes said container for non-use of the device; and a suction pad detachably arranged on said cover and movable together therewith between said positions so that in said closed position when said suction pad contacts said wick the solving medium flows from said wick into said suction pad under the action of suction and flushes particles of cosmetic substance adhered to said wick whereby said wick is cleansed, and then when said cover is moved from said closed position to said open position said suction pad is removed from said container together into said cover.

2. A device for wetting skin with a solving medium before or after application of a pin-shaped coloring cosmetic substance, the device comprising a container;

a tampon soaked with a solving medium and accommodated in said container;

a wick arranged in a liquid-conducting communication with said tampon and extending outwardly beyond said container;

a sealingly closing cover removable from said container for use of the device; and a suction pad arranged on said cover so that when said suction pad contacts said wick the solving medium flows from said wick into said suction pad under the action of suction and flushes particles of cosmetic substance adhered to said wick whereby said wick is cleansed.

3. A device as defined in claim 2, wherein said wick has a portion extending outwardly beyond said container and having a tip of an inclined wedge-like shape.

4. A device as defined in claim 2, wherein said wick is so arranged that it can be exchanged.

5. A portion as defined in claim 2, wherein said cover has an upper end side, said suction pad being mounted on said upper end side of said cover.

* * * * *